United States Patent
Mazor et al.

(10) Patent No.: US 9,551,677 B2
(45) Date of Patent: Jan. 24, 2017

(54) ANGLE CALIBRATION FOR GRAZING-INCIDENCE X-RAY FLUORESCENCE (GIXRF)

(71) Applicant: JORDAN VALLEY SEMICONDUCTORS LTD., Migdal HaEmek (IL)

(72) Inventors: Isaac Mazor, Haifa (IL); Asher Peled, Kfar-Vradim (IL)

(73) Assignee: BRUKER JV ISRAEL LTD., Migdal Haemek (IL)

( * ) Notice: Subject to any disclaimer, the term of this patent is extended or adjusted under 35 U.S.C. 154(b) by 209 days.

(21) Appl. No.: 14/555,613

(22) Filed: Nov. 27, 2014

(65) Prior Publication Data
US 2015/0204806 A1    Jul. 23, 2015

Related U.S. Application Data

(60) Provisional application No. 61/929,556, filed on Jan. 21, 2014.

(51) Int. Cl.
*G01N 23/223* (2006.01)

(52) U.S. Cl.
CPC ......... *G01N 23/223* (2013.01); *G01N 2223/61* (2013.01); *G01N 2223/6116* (2013.01)

(58) Field of Classification Search
CPC .......................... G01N 23/223; G01N 23/207; G01N 23/2076; G01N 23/22; G01N 23/20; G01N 23/2206; G01N 2223/076; G21K 1/06; G21K 1/062; A61B 6/485
USPC .......................... 378/44, 45, 46, 50, 70, 207
See application file for complete search history.

(56) References Cited

U.S. PATENT DOCUMENTS

| | | |
|---|---|---|
| 4,725,963 A | 2/1988 | Taylor et al. |
| 5,151,588 A | 9/1992 | Kiri et al. |
| 5,574,284 A | 11/1996 | Farr |
| 5,619,548 A | 4/1997 | Koppel |
| 5,740,226 A | 4/1998 | Komiya et al. |
| 5,923,720 A | 7/1999 | Barton et al. |
| 5,949,847 A | 9/1999 | Terada et al. |
| 6,192,103 B1 | 2/2001 | Wormington et al. |
| 6,381,303 B1 | 4/2002 | Vu et al. |
| 6,389,102 B2 | 5/2002 | Mazor et al. |
| 6,453,006 B1 | 9/2002 | Koppel et al. |
| 6,507,634 B1 | 1/2003 | Koppel et al. |
| 6,512,814 B2 | 1/2003 | Yokhin et al. |
| 6,535,575 B2 | 3/2003 | Yokhin |
| 6,643,354 B2 | 11/2003 | Koppel et al. |
| 6,680,996 B2 | 1/2004 | Yokhin et al. |

(Continued)

OTHER PUBLICATIONS

Jaklevic et al., "Energy Dispersive X-Ray Fluorescence Analysis Using Pulsed X-Ray Tube Excitation", Advances in X-Ray Analysis, vol. 19, pp. 266-275, 1976.

(Continued)

*Primary Examiner* — Jurie Yun
(74) *Attorney, Agent, or Firm* — D. Kligler IP Services Ltd.

(57) ABSTRACT

A method includes directing an X-ray beam to be incident at a grazing angle on a location on a surface of the sample. An X-ray fluorescence excited at the location is measured. A reflection angle of the X-ray beam from the surface and a transmission angle of the X-ray beam are measured. An angle of incidence of the X-ray beam on the surface is evaluated using the measured reflection and transmission angles, and the measured X-ray fluorescence is analyzed using the evaluated angle of incidence.

20 Claims, 3 Drawing Sheets

(56) References Cited

U.S. PATENT DOCUMENTS

| | | |
|---|---|---|
| 6,711,232 B1 | 3/2004 | Janik |
| 6,744,950 B2 | 6/2004 | Aleksoff |
| 6,768,785 B2 | 7/2004 | Koppel et al. |
| 6,771,735 B2 | 8/2004 | Janik et al. |
| 6,813,338 B2 | 11/2004 | Takata et al. |
| 6,987,832 B2 | 1/2006 | Koppel et al. |
| 2001/0028699 A1 | 10/2001 | Iwasaki |
| 2001/0043668 A1 | 11/2001 | Hayashi et al. |
| 2002/0097837 A1 | 7/2002 | Fanton et al. |
| 2003/0157559 A1 | 8/2003 | Omote et al. |

OTHER PUBLICATIONS

Holy et al., "High Resolution X-Ray Scattering from Thin Films and Multilayers", Springer Verlag, chapter 2.1 (pp. 18-21), year 1999.

Parrill et al., "GISAXS—Glancing incidence small angle X-ray scattering", Journal De Physique IV, vol. 3, pp. 411-417, Dec. 1993.

Wormington et al., "Characterization of Porous, Low-A; Dielectric Thin-Films using X-ray Reflectivity", Bede Scientific Inc, Characterization and Metrology for VLSI Technology: International Conference, pp. 651-655, 2003.

Wu et al., "Substepping and its Application to HST Imaging", Astronomical Data Analysis Software and Systems VII, ASP Conference Series, vol. 145, pp. 82-85, 1998.

Chihab et al., "New Apparatus for Grazing X-Ray Reflectometry in the Angel-Resolved Dispersive Mode", Journal of Applided Cystallography, vol. 22, p. 460-464, 1989.

Wiener et al., "Characterization of titanium nitride layers by grazing-emission X-ray fluorescence spectrometry", Applied Surface Science, vol. 125, issue 2, pp. 129-136, Feb. 1998.

Spear, J., "Metrology for Low-k Materials", Silknet Alliance, 21 pages, year 2003.

Series 5000 Model XTF5011 X-ray Tube Information, Oxford Instruments Inc, Scotts Valley, CA, USA, 3 pages, Jun. 1998.

X-Ray Optical Systems, Inc., "Monolithis polycapillary lens information", 2 pages, Dec. 29, 1998.

ANGLE CALIBRATION FOR GRAZING-INCIDENCE X-RAY FLUORESCENCE (GIXRF)

CROSS-REFERENCE TO RELATED APPLICATIONS

This application claims the benefit of U.S. Provisional Patent Application 61/929,556, filed Jan. 21, 2014, whose disclosure is incorporated herein by reference.

FIELD OF THE INVENTION

The present invention relates generally to X-ray analysis, and particularly to methods and systems for analysis of thin film layers deposited on a sample.

BACKGROUND OF THE INVENTION

Various X-ray techniques, such as grazing-incidence X-ray fluorescence (GIXRF), are used for materials characterization in many fields, including in semiconductor devices. Examples of prior art techniques are provided below.

U.S. Pat. No. 6,381,303, to Vu, et al., whose disclosure is incorporated herein by reference, describes an X-ray microanalyzer for thin films, which irradiates a spot having a dimension less than 500 μm on a surface of the sample. A first X-ray detector captures fluorescent X-rays emitted from the sample, responsive to the irradiation, at a high angle relative to the surface of the sample. A second X-ray detector captures X-rays from the spot at a grazing angle relative to the surface of the sample. Processing circuitry receives respective signals from the first and second X-ray detectors responsive to the X-rays captured thereby, and analyzes the signals in combination to determine a property of a surface layer of the sample within the area of the spot.

U.S. Pat. No. 6,829,327, to Chen, et al., whose disclosure is incorporated herein by reference, describes an improved total-reflection X-ray fluorescence (TXRF) apparatus using a doubly-curved optic for use in detecting foreign matter on surfaces, such as, on semiconductor wafers.

U.S. Pat. No. 7,039,158, to Janik, et al., whose disclosure is incorporated herein by reference, describes a thin film analysis system which includes multi-technique analysis capability. Grazing incidence X-ray reflectometry (GXR) can be combined with X-ray fluorescence (XRF) using an electron beam to excite X-rays that are measured with a wavelength-dispersive X-ray spectrometry (WDX) detectors to obtain accurate thickness measurements with GXR and high-resolution composition measurements with XRF using WDX detectors.

U.S. Pat. No. 6,108,398, to Mazor, et al., whose disclosure is incorporated herein by reference, describes an X-ray fluorescent analyzer and method for analyzing a sample, including an X-ray beam generator, which generates an X-ray beam incident at a spot on the sample, and creates a plurality of fluorescent X-ray photons. There are a plurality of semiconducting detectors arrayed around the spot so as to capture the fluorescent X-ray photons and in response produce a plurality of electrical pulses suitable for analysis of the sample.

U.S. Pat. No. 7,062,013, to Berman, et al., whose disclosure is incorporated herein by reference, describes a method for inspection of a sample that includes a first layer having a known reflectance property and a second layer formed over the first layer. The method includes directing radiation toward a surface of the sample and sensing the radiation reflected from the surface so as to generate a reflectance signal as a function of elevation angle relative to the surface.

U.S. Pat. No. 7,258,485, to Nakano, et al., whose disclosure is incorporated herein by reference, describes an X-ray thin film inspection apparatus including a sample table on which an inspection target such as a product wafer or the like is mounted, a positioning mechanism for moving the sample table, a goniometer having first and second swing arms, at least one X-ray irradiation unit that are mounted on the first swing arm and containing an X-ray tube and an X-ray optical element in a shield tube, an X-ray detector mounted on a second swing arm, and an optical camera for subjecting the inspection target disposed on the sample table to pattern recognition.

U.S. Pat. No. 6,173,036, to Hossain, et al., whose disclosure is incorporated herein by reference, describes Depth profile metrology using grazing incidence X-ray fluorescence. A series of X-ray fluorescence measurements are performed at varying small angles and analyzed for depth profiling of elements within a substrate.

Further theory and details of GIXRF are provided by Klockenkämper, in "Total Reflection X-ray Fluorescence Analysis," John Wiley & Sons, 1997, chapters 2-4, which is incorporated herein by reference.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention that is described herein provides a method including directing an X-ray beam to be incident at a grazing angle on a location on a surface of the sample. An X-ray fluorescence excited at the location is measured. A reflection angle of the X-ray beam from the surface and a transmission angle of the X-ray beam are measured. An angle of incidence of the X-ray beam on the surface is evaluated using the measured reflection and transmission angles, and the measured X-ray fluorescence is analyzed using the evaluated angle of incidence.

In some embodiments, directing the X-ray beam includes focusing the X-ray beam so as to converge on the surface of the sample. In other embodiments, measuring the transmission angle includes assessing the transmission angle while the sample is not present. In yet other embodiments, measuring the transmission angle includes assessing the transmission angle of the X-ray beam through the sample.

In an embodiment, measuring the reflection and transmission angles includes positioning an array detector perpendicular to the surface of the sample, and configuring the array detector to sense a reflection of the X-ray beam from the surface and to sense a transmission of the X-ray beam. In another embodiment, evaluating the angle of incidence includes averaging the measured reflection and transmission angles to determine an angular deviation of the surface relative to a mean plane thereof. In yet another embodiment, evaluating the angle of incidence includes calculating an actual angle of incidence by summing the angular deviation of the surface and a nominal incident angle to the surface.

In some embodiments, analyzing the measured X-ray fluorescence includes finding a corrected intensity of the X-ray fluorescence in terms of the measured X-ray fluorescence, the actual angle of incidence and the nominal incident angle. In other embodiments, measuring and analyzing the X-ray fluorescence are performed using the X-ray beam used for evaluating the angle of incidence. In yet other embodiments, measuring and analyzing the X-ray fluorescence are performed using a second X-ray beam, which has a known angular offset relative to the X-ray beam used for evaluating the angle of incidence.

There is additionally provided, in accordance with an embodiment of the present invention, an apparatus including an X-ray source, first and second detectors, and a processor. The X-ray source is configured to generate and direct an X-ray beam to be incident at a grazing angle on a location on a surface of a sample. The first detector is configured to measure X-ray fluorescence excited at the location by the X-ray beam. The second detector is configured to sense a reflection of the X-ray beam from the surface and a transmission of the X-ray beam. The processor is configured to measure a reflection angle of the reflection and a transmission angle of the transmission, to evaluate an angle of incidence of the X-ray beam on the surface using the measured reflection and transmission angles, and to analyze the measured X-ray fluorescence using the evaluated angle of incidence.

The present invention will be more fully understood from the following detailed description of the embodiments thereof, taken together with the drawings in which:

DETAILED DESCRIPTION OF EMBODIMENTS

Overview

Figure 1:
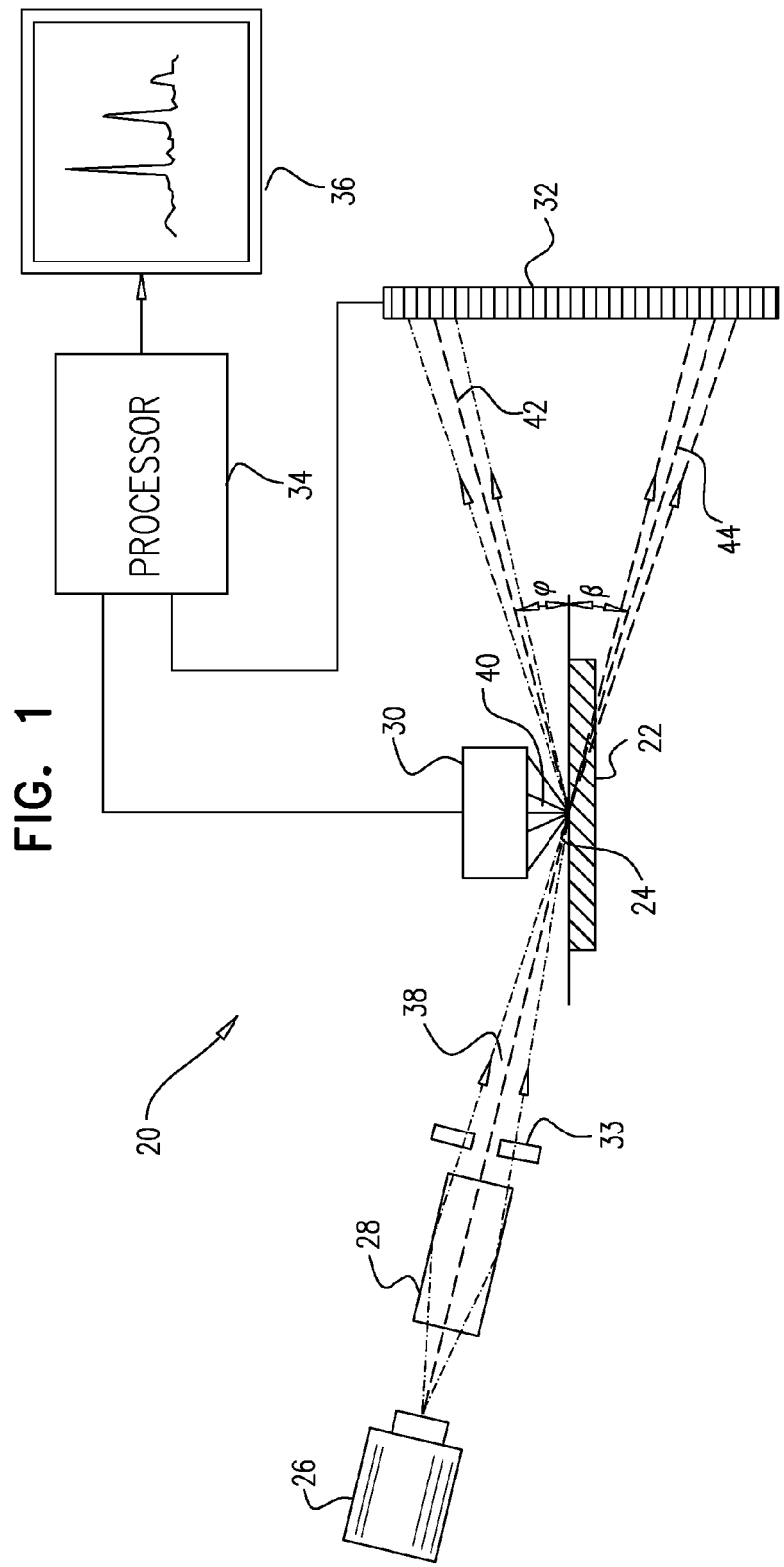
FIG. 1 is a schematic side view of a sample, such as a semiconductor wafer, under a grazing-incidence X-ray fluorescence (GIXRF) measurement system, in accordance with an embodiment of the present invention.

Grazing-incidence X-ray fluorescence (GIXRF) is a technique for measurement and analysis that can be used for depth-profiling and characterization of thin film layers, typically in the thickness range from a few hundred nanometers down to a few nanometers.

In GIXRF, the exciting X-ray beam is incident on the sample at grazing angles, i.e., angles nearly parallel to the surface, near or below the angle of total external reflection, which is typically less than 1° for most materials and hard X-rays.

In GIXRF, the exciting X-ray beam has a much reduced depth of penetration into the sample as compared with beams with much higher incident angles. The intensity of the fluorescent radiation emitted by atoms that are excited by the X-ray beam is proportional to the wave field intensity. As the spatial distribution and depth of the wave field within the sample depend sensitively on the incident angle of the X-ray beam, it is generally important to control this angle accurately in order to obtain meaningful measurements of the structure and composition of the upper layer of the sample.

GIXRF has been applied (as described in above-referenced U.S. Pat. No. 6,173,036, for example) in making measurements on semiconductor wafers. Such wafers, however, may be deformed, for example, due to stresses from deposited thin-films and/or thermal processing. Therefore, for accurate GIXRF measurement, it is desirable that the angle of incidence of the exciting X-ray beam be measured precisely at each point on the wafer on which it is incident. Such considerations are similarly of concern in GIXRF measurements on samples of other sorts whose flatness cannot be guaranteed.

Embodiments of the present invention that are described hereinbelow measure the angles of reflection and transmission of the exciting X-ray beam in order to accurately find a "zero-angle" of a wafer or other sample under GIXRF measurement. The zero angle in this context means the angle of a tangent to the surface of the sample at the location at which the exciting X-ray beam is incident on the surface, wherein the tangent is taken in a plane normal to the surface that contains the incident beam. The terms "zero-angle" and "angular deviation" are used interchangeably in the present patent application.

Measurement of the angle of reflection of the exciting X-ray beam relative to this zero-angle gives an accurate indication of the actual angle of incidence of the beam on the sample. In some embodiments the exciting X-ray beam itself is used in the zero-angle measurement, in which case the calibration is highly precise and, at the same time, can be performed at minimal added cost in terms of measurement equipment and throughput. In an alternative embodiment, a first X-ray source may be used to calibrate the incidence angle of a second X-ray source, assuming a fixed angular offset between the two sources. For example, a system may comprise a Cu source to measure low energies and a Mo source to measure higher energies, and the beam of the Cu source may be used to calibrate the incidence angle of the Mo source.

In the disclosed embodiments, a GIXRF system comprises an X-ray source, which is configured to generate and direct an X-ray beam to be incident at a grazing angle on a location on a surface of a sample. In an embodiment, the X-ray beam is a converging beam that is focused on the incidence point on the sample. This feature enables the system to perform rapid alignment, since it eliminates the need for scanning a parallel incident beam over a range of incidence angles. The system further comprises two detectors: one detector configured to measure the X-ray fluorescence excited at the location by the X-ray beam, and another detector configured to sense a reflection of the X-ray beam from the surface, and to sense a transmission of the X-ray beam through the sample.

Additionally, the system comprises a processor, which is configured to measure a reflection angle of the reflection and a transmission angle of the transmission, to calibrate an angle of incidence of the X-ray beam on the surface using the measured reflection and transmission angles, and to analyze the measured X-ray fluorescence using the calibrated angle of incidence at each measured location on the sample. The described system and method provide a fast and accurate calibration of the incident beam for GIXRF applications, as will be apparent to those skilled in the art after reading the present description.

The present invention is applicable to various applications, such as characterizing semiconductor wafers, and thus, the terms "wafer" and "sample" are used interchangeably in the present patent application.

System Description

FIG. 1 is a schematic side view of a sample, such as a semiconductor wafer 22, under a grazing-incidence X-ray fluorescence (GIXRF) measurement system 20, in accordance with an embodiment of the present invention.

System 20 comprises one or more X-ray sources 26, such as a TF5011 manufactured by Oxford X-ray Technology (Scotts Valley, Calif.) or a MCBM 50-0, 6B, MCBM 65B-50, MCBM 50G-50 manufactured by rtw RÖNTGEN-TECHNIK DR. WARRIKHOFF GmbH & Co. (Berlin, Germany).

In an embodiment, multiple X-ray sources 26, each comprising a different anode, may optionally be provided to generate different X-ray energies. The different X-ray energies may be used for excitation of different elements in the wafer.

System 20 further comprises X-ray optics 28, which collect an emitted X-ray beam 38 originating from source 26. Optics 28 adjust the characteristics of beam 38 to a desired specification focused, via one or more motorized slits 33 (made of an X-ray opaque material whose position and size can be adjusted independently), on the surface of wafer 22 at a measurement area 24. Such optics may include, but are not limited to doubly curved crystal (DCC) optics manufactured by X-ray Optical Systems Inc. (Albany, N.Y.), and multilayer mirror optics, such as FOX 3D series manufactured by Xenocs SA (Grenoble, France) or ASTIX series manufactured by AXO DRESDEN GmbH (Dresden, Germany).

In FIG. 1, beam 38 is incident on wafer 22 at grazing angles, i.e., angles nearly parallel to the surface, near or below the angle of total external reflection. For most materials and hard X-rays, although not necessarily, the grazing angle is below 1°. In the present example beam 38 is a converging beam focused on the sample.

GIXRF techniques are typically used for near-surface measurement and characterization of semiconductor wafers 22, however such wafers 22 are prone to bending. In order to perform accurate GIXRF measurements, it is desirable that the angle of incidence of beam 38 is adapted accurately according to the surface at each measurement area 24.

Source 26, optics 28 and slits 33 are mounted on one or more motorized arms that can be rotated about an axis parallel to the surface of wafer 22 to adjust the range of angles illuminated by the convergent X-ray beam. The source, the optics and the slits may be mounted on a single arm so that they move together. Alternatively, the source and the optics and slits may be mounted on two separate arms that can be independently adjusted. Wafer 22 is mounted on a motorized table that can be used to set the position of wafer 22 in the horizontal plane (xy), as well as the azimuth rotation φ of the wafer about an axis perpendicular to the wafer surface.

A position sensitive X-ray detector 32, which is an array detector, is adapted to sense a reflection of an X-ray beam 42 from the surface and a transmission of an X-ray beam 44 through the sample. Such detectors include, but are not limited to, a CCD/CMOS camera or a linear (1D) Si pin-diode array such as the Mythen series of detectors from DECTRIS Ltd (Baden, Switzerland).

An energy dispersive X-ray fluorescence (EDXRF) detector 30 is located in close proximity to, and is typically parallel to, the surface of wafer 22. The detector is typically mounted above the point of incidence of beam 38 at area 24 of wafer 22, and may be coupled to a rangefinder, such as a suitable optical rangefinder, for measuring the distance to the wafer surface accurately and precisely. Such detectors 30 include Si(Li) or silicon-drift detectors (SDDs) such as the AXAS or VITUS series of detectors manufactured by Ketek Munich, Germany or those commercially available from other suppliers and preferably have a large active area so that they capture a large solid angle of radiation emitted from the surface of wafer 22. Detector 30 may include a collimator to reduce background scattering from wafer 22 and its environment. Detector 30 collects EDXRF signals 40 from wafer 22.

A processor 34 collects output signals from detectors 32 and 30. As will be explained in detail below, processor uses the signals from detector 32 to measure the reflection and transmission angles at area 24. Furthermore, processor 34 uses these angles to calibrate the angle of incidence of beam 38 on the surface. Subsequently, processor 34 analyzes X-ray fluorescence signals 40 using the calibrated angle of incidence.

Typically, processor 34 comprises a general-purpose computer, which is programmed in software to carry out the functions described herein. The software may be downloaded to the processor in electronic form, over a network, for example, or it may, alternatively or additionally, be provided and/or stored on non-transitory tangible media, such as magnetic, optical, or electronic memory.

Detector 32 detects two spatial peaks of signals, one peak corresponds to the center of reflected beam 42, and the other peak, to the center of transmitted beam 44. In some embodiments, transmitted beam 44 is a beam that penetrates and traverses through the sample. In other embodiments, transmitted beam 44 is a direct beam that reaches the detector when the sample is not present, i.e., a continuation of the incident beam. For example, the transmitted beam may be measured once before the sample is loaded, whereas the reflected beam may be measured at every desired location on the sample surface. The disclosed techniques can be used in both manners. In the context of the present patent application and in the claims, the term "transmitted beam" is used to describe both cases. The transmitted beam is also referred to herein as a direct beam.

In other words, in some embodiments detector 32 detects the peak of beam 44 when the sample is present. In other embodiments the detector detects the peak of the direct (incident) beam when the sample is not present, in order to define the position of the incident beam as a reference angle.

The peaks of beams 42 and 44 may be identified by processor 34, and the processor may also provide a graphic output of the peaks on a display 36. The known pitch of the array of detector 32, and the known distance of detector 32 from the center of beam 38 at area 24, are used by processor 34 to convert the two peak locations into respective angles, φ (angle of reflection) and β (angle of transmission), above and below a mean plane of the wafer. The average of these two angles provides the zero angle, or angular deviation, of the surface, according to equation (1).

$$\delta = \frac{\varphi + \beta}{2} \tag{1}$$

where φ is the angle of reflection,
β is the angle of the direct beam,
δ is the angular deviation,
and where φ, β, δ are positive or negative angles measured relative to the mean plane of the wafer.

As is explained with reference to FIG. 2 below, angular deviation δ provides a correction between a nominal incident angle of beam 38 and an actual, precise angle of incidence of the beam.

Figure 2:
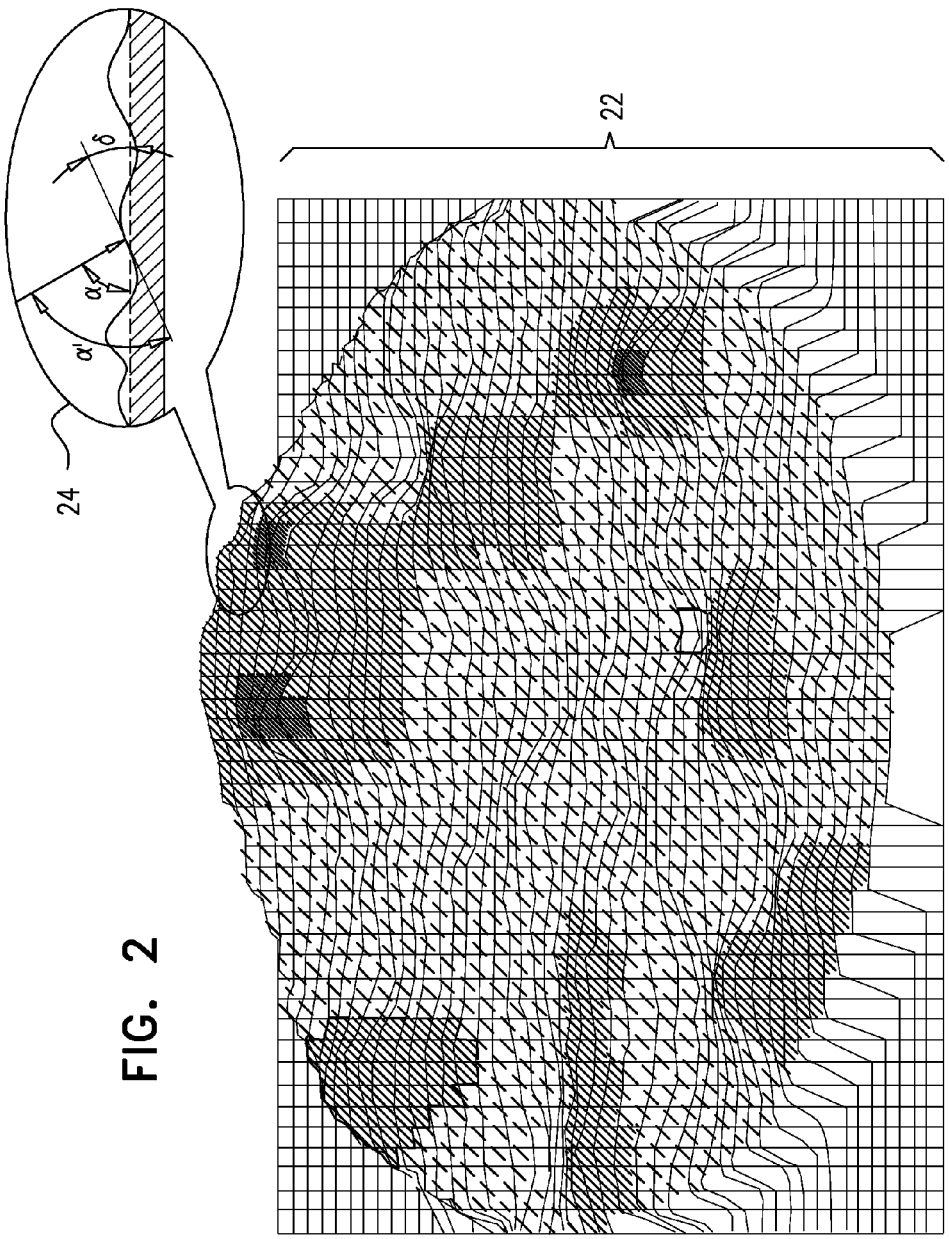
FIG. 2 is a schematic pictorial illustration of a topography map of a wafer, in accordance with an embodiment of the present invention.

FIG. 2 is a schematic pictorial illustration of a topography map of wafer 22, in accordance with an embodiment of the present invention.

Typically, the surface of wafer 22 varies in height as a result of semiconductor processes. The inset illustrates a cross-section of area 24. A wavy line drawn in the inset illustrates the surface topography of area 24 while a straight dashed line illustrates a mean plane of the wafer surface. A nominal incident angle α is measured with respect to the mean plane, and the surface has an angular deviation, angle δ, which measures the actual deviation of the surface from the mean plane at area 24. Angle δ is measured as described above with reference to equation (1) and δ (x,y) is a function of the position (x,y) across wafer 22.

As is apparent by inspection of the inset of FIG. 2, $$\alpha' = \alpha + \delta \quad (2)$$

where α' is the actual angle of incidence of beam 38.

In some embodiments, angle α' is used in a physical model to estimate the depth and area of penetration of the X-ray beam into the surface layer of wafer 22, and thus to extract from X-ray fluorescence signals 40 accurate measurements of the composition and structure of the surface layer.

Incident beam 38, at angles below a critical angle of external reflection for X-rays, creates reflections of most of the excitation beam photons at this surface. At angles near the critical angle for total external reflection, the fluorescence intensity is roughly proportional to the incident angle of the X-ray beam on the sample. In other embodiments, the angular deviation δ of the surface that is measured in the above manner may be applied in computing a corrected intensity $I_{Corrected}$ of the incident beam relative to a reference intensity $I_{Ref}$ that was measured at a known nominal angle α, using equation (3):

$$I_{Corrected}(\alpha') = I_{Ref}(\alpha) \frac{\sin(\alpha')}{\sin(\alpha)} \quad (3)$$

From equation (2), equation (3) may be rewritten:

$$I_{Corrected}(\alpha + \delta) = I_{Ref}(\alpha) \frac{\sin(\alpha + \delta)}{\sin(\alpha)} \quad (4)$$

In some embodiments, the measured fluorescence of the sample may be corrected by the proportionalities of equations (3) or (4) in order to extract an accurate estimate of the elemental composition of the upper layer of the sample. Alternatively or additionally, the angular correction may be applied in substantially any other suitable fashion. For example, equations (3) or (4) may be modified so that the proportionality is between intensities and incident angles, rather than intensities and sines of the incident angles. As another example, processor 34 may move the source and optics mechanically so as to physically set the desired incident angle at each measurement point across the wafer. This assumes that the source and optics are on a motorized and computer controlled rotation stage that can be controlled by processor 34.

In yet other embodiments, the system configuration in FIG. 1 may be used in other measurement protocols, to provide more precise and faster analysis of the properties of thin films, while reducing the need for external calibration standards. The combination of GIXRF with X-ray reflectivity (XRR) can be useful, for example, in removing correlations in the analysis (modelling) of complex stacks, such as measuring the thickness of a layer of MgO that is less than 1 nm thick from the intensity of the Mg Kα emission line and feeding this information into the XRR analysis from a complex multilayer stack used in the manufacturing of read-heads in the magnetic recording industry. Modelling of XRR data is addressed, for example, in U.S. Pat. Nos. 7,103,142 and 7,130,376, whose disclosure is incorporated herein by reference.

Figure 3:
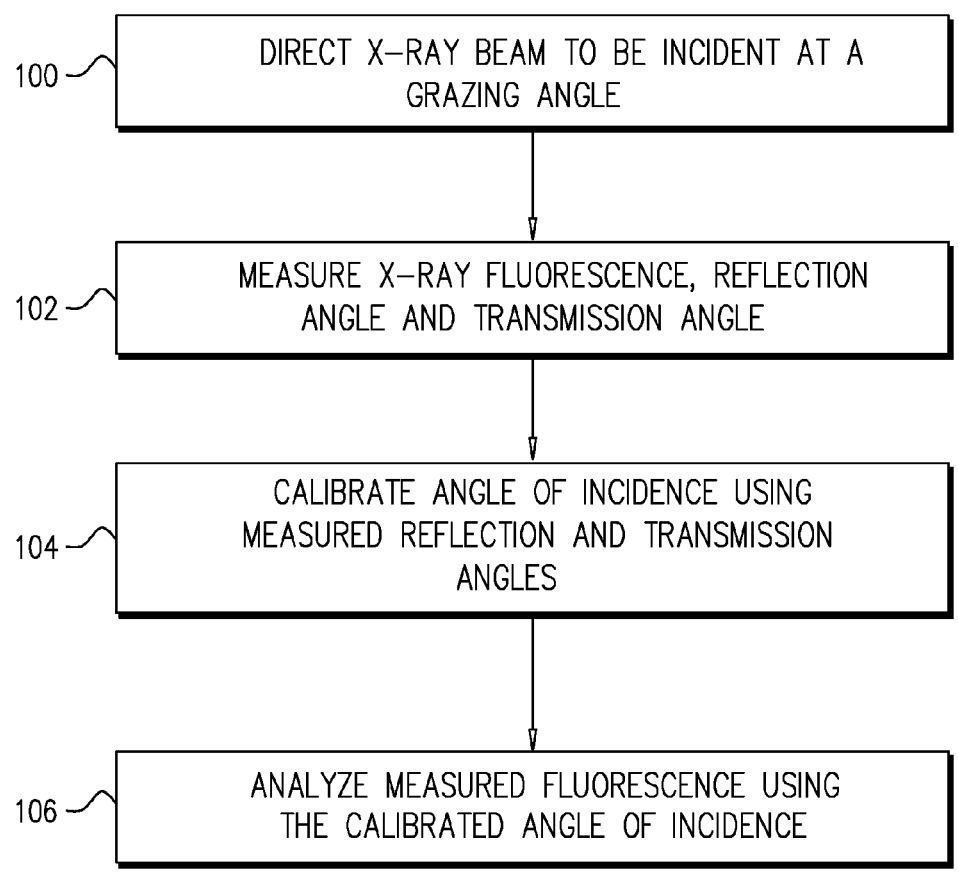
FIG. 3 is a flow chart that schematically illustrates a method for angle calibration in a GIXRF system, in accordance with an embodiment of the present invention.

FIG. 3 is a flow chart that schematically illustrates a method for angle calibration in a GIXRF system 20, in accordance with an embodiment of the present invention.

The method begins at an X-ray beam direction step 100, wherein system 20 directs the X-ray beam to be incident on area 24 at a grazing angle. At a measurement step 102, system 20 measures X-ray fluorescence 40 with detector 30, and uses detector 32 to detect the reflected and transmitted beams. Processor 34 receives signals from detector 32 to measure the reflection and transmission angle, respectively. From the measured angles, the processor evaluates the angular deviation δ at area 24, using equation (1). The terms "calculate" and "evaluate" are used interchangeably in the present patent application.

At an incident beam calibration step 104, system 20 uses angle δ to find a corrected angle of incidence α' of beam 38, as explained above with reference to equation (2).

At an analysis step 106, system 20 calculates a corrected value for the fluorescent X-ray intensity, according to equations (3) or (4), and the value of the corrected angle of incidence from step 104, and uses the corrected intensity to analyze the measured fluorescence.

Although the embodiments described herein refer mainly to semiconductor metrology applications and GIXRF, the principles of the disclosed techniques can be used, mutatis mutandis, in various other applications in which thin films are deposited on a substrate.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A method for analysis of a sample, comprising:
   directing an X-ray beam to be incident at a grazing angle on a location on a surface of the sample;
   measuring X-ray fluorescence excited at the location;
   measuring a reflection angle of the X-ray beam from the surface and a transmission angle of the X-ray beam;
   evaluating an angle of incidence of the X-ray beam on the surface using the measured reflection and transmission angles; and
   analyzing the measured X-ray fluorescence using the evaluated angle of incidence.

2. The method according to claim 1, wherein directing the X-ray beam comprises focusing the X-ray beam so as to converge on the surface of the sample.

3. The method according to claim 1, wherein measuring the transmission angle comprises assessing the transmission angle while the sample is not present.

4. The method according to claim 1, wherein measuring the transmission angle comprises assessing the transmission angle of the X-ray beam through the sample.

5. The method according to claim 1, wherein measuring the reflection and transmission angles comprises positioning an array detector perpendicular to the surface of the sample, and configuring the array detector to sense a reflection of the X-ray beam from the surface and to sense a transmission of the X-ray beam.

6. The method according to claim 1, wherein evaluating the angle of incidence comprises averaging the measured reflection and transmission angles to determine an angular deviation of the surface relative to a mean plane thereof.

7. The method according to claim 6, wherein evaluating the angle of incidence comprises calculating an actual angle of incidence by summing the angular deviation of the surface and a nominal incident angle to the surface.

8. The method according to claim 7, wherein analyzing the measured X-ray fluorescence comprises finding a corrected intensity of the X-ray fluorescence in terms of the measured X-ray fluorescence, the actual angle of incidence and the nominal incident angle.

9. The method according to claim 1, wherein measuring and analyzing the X-ray fluorescence are performed using the X-ray beam used for evaluating the angle of incidence.

10. The method according to claim 1, wherein measuring and analyzing the X-ray fluorescence are performed using a second X-ray beam, which has a known angular offset relative to the X-ray beam used for evaluating the angle of incidence.

11. Apparatus, comprising:
an X-ray source, which is configured to generate and direct an X-ray beam to be incident at a grazing angle on a location on a surface of a sample;
a first detector, which is configured to measure X-ray fluorescence excited at the location by the X-ray beam;
a second detector, which is configured to sense a reflection of the X-ray beam from the surface and a transmission of the X-ray beam; and
a processor, which is configured to measure a reflection angle of the reflection and a transmission angle of the transmission, to evaluate an angle of incidence of the X-ray beam on the surface using the measured reflection and transmission angles, and to analyze the measured X-ray fluorescence using the evaluated angle of incidence.

12. The apparatus according to claim 11, wherein the X-ray source is configured to focus the X-ray beam so as to converge on the surface of the sample.

13. The apparatus according to claim 11, wherein the second detector is configured to sense the transmission of the X-ray beam while the sample is not present.

14. The apparatus according to claim 11, wherein the second detector is configured to sense the transmission of the X-ray beam through the sample.

15. The apparatus according to claim 11, wherein the second detector comprises an array detector positioned perpendicularly to the surface of the sample, and configured to sense the reflection of the X-ray beam from the surface and the transmission of the X-ray beam.

16. The apparatus according to claim 11, wherein the processor is configured to average the measured reflection and transmission angles so as to determine an angular deviation of the surface relative to a mean plane thereof.

17. The apparatus according to claim 16, wherein the processor is configured to calculate an actual angle of incidence by summing the angular deviation of the surface and a nominal incident angle to the surface.

18. The apparatus according to claim 17, wherein the processor is configured to find a corrected intensity of the X-ray fluorescence in terms of the measured X-ray fluorescence, the actual angle of incidence and the nominal incident angle.

19. The apparatus according to claim 11, wherein the first detector is configured to measure the X-ray fluorescence and the processor is configured to analyze the X-ray fluorescence using the X-ray beam used for evaluating the angle of incidence.

20. The apparatus according to claim 11, wherein the X-ray source is further configured to generate and direct a second X-ray beam, which has a known angular offset relative to the X-ray beam used for evaluating the angle of incidence, and wherein the first detector is configured to measure the X-ray fluorescence and the processor is configured to analyze the X-ray fluorescence using the second X-ray beam.

* * * * *